(12) United States Patent
Dalla Pria et al.

(10) Patent No.: US 10,918,490 B2
(45) Date of Patent: Feb. 16, 2021

(54) ACETABULAR PROSTHESIS

(71) Applicant: LIMACORPORATE S.P.A., San Daniele del Friuli (IT)

(72) Inventors: Paolo Dalla Pria, Udine (IT); Luca Giorgini, Artegna (IT); Michele Pressacco, Udine (IT)

(73) Assignee: LIMACORPORATE SPA, San Daniele del Friuli (IT)

( * ) Notice: Subject to any disclaimer, the term of this patent is extended or adjusted under 35 U.S.C. 154(b) by 0 days.

(21) Appl. No.: 14/893,900

(22) PCT Filed: May 26, 2014

(86) PCT No.: PCT/IB2014/061719
§ 371 (c)(1),
(2) Date: Nov. 24, 2015

(87) PCT Pub. No.: WO2014/188400
PCT Pub. Date: Nov. 27, 2014

(65) Prior Publication Data
US 2016/0106542 A1   Apr. 21, 2016

(30) Foreign Application Priority Data

May 24, 2013   (IT) .......................... UD2013A000074

(51) Int. Cl.
*A61F 2/34*   (2006.01)
*A61F 2/30*   (2006.01)

(52) U.S. Cl.
CPC ....... *A61F 2/34* (2013.01); *A61F 2002/30112* (2013.01); *A61F 2002/30331* (2013.01);
(Continued)

(58) Field of Classification Search
CPC ................ A61F 2/34; A61F 2002/3441; A61F 2002/3448; A61F 2002/3414;
(Continued)

(56) References Cited

U.S. PATENT DOCUMENTS

| 4,944,717 A | * | 7/1990 | Georget | ................... F16G 5/20 |
| | | | | 474/238 |
| 5,549,695 A | * | 8/1996 | Spotorno | .................. A61F 2/34 |
| | | | | 623/22.23 |

(Continued)

FOREIGN PATENT DOCUMENTS

EP   1 825 834 A1   8/2007

OTHER PUBLICATIONS

Search Report and Written Opinion for PCT/IB2014/061719, dated Aug. 18, 2014.

*Primary Examiner* — Bruce E Snow
*Assistant Examiner* — Melissa A Hoban
(74) *Attorney, Agent, or Firm* — Marshall, Gerstein & Borun LLP (57) ABSTRACT

Acetabular prosthesis comprising an acetabular cup, an acetabular insert, able to be stably coupled inside the acetabular cup and configured to receive an articulation head and a centering unit configured to guide and center the insertion and stable positioning of the acetabular insert in the acetabular cup. The centering unit comprises a centering hole provided in the acetabular cup and a centering pin provided on the acetabular insert and which develops along a centering axis, configured to be inserted in the centering hole. The centering pin is provided with an external lateral surface that has an undulating development along the centering axis.

11 Claims, 4 Drawing Sheets

(52) U.S. Cl.
CPC ............... *A61F 2002/30332* (2013.01); *A61F 2002/30337* (2013.01); *A61F 2002/3401* (2013.01); *A61F 2002/3414* (2013.01)

(58) Field of Classification Search
CPC ...... A61F 2002/3411; A61F 2002/3668; A61F 2002/30135; A61F 2002/30136
See application file for complete search history.

(56) References Cited

U.S. PATENT DOCUMENTS

| | | | | |
|---|---|---|---|---|
| 5,879,401 | A * | 3/1999 | Besemer | A61F 2/4684 623/22.28 |
| 6,379,389 | B1 * | 4/2002 | Koch | A61F 2/34 623/22.15 |
| 7,267,693 | B1 | 9/2007 | Mandell et al. | |
| 2008/0046083 | A1 * | 2/2008 | Hewko | A61F 2/4425 623/17.16 |
| 2008/0306606 | A1 * | 12/2008 | Shields | A61F 2/34 623/22.21 |
| 2010/0131073 | A1 * | 5/2010 | Meridew | A61F 2/34 623/22.28 |
| 2010/0174380 | A1 * | 7/2010 | Lewis | A61F 2/32 623/22.11 |
| 2012/0101590 | A1 | 4/2012 | Preuss et al. | |
| 2013/0079885 | A1 * | 3/2013 | Meier | A61F 2/38 623/20.21 |

* cited by examiner fig. 3 fig. 4 fig. 5 fig. 6 fig. 7 fig. 8

US 10,918,490 B2

ACETABULAR PROSTHESIS

FIELD OF THE INVENTION

The present invention concerns an acetabular prosthesis, to be used in a hip prosthesis, comprising an acetabular cup and an acetabular insert to be positioned in the acetabular cup and in which the head of the femur and corresponding femoral prosthesis can articulate.

BACKGROUND OF THE INVENTION

In the field of hip prostheses, a prosthetic element is known, formed by coupling an acetabular cup and an acetabular insert with a semi-spherical cavity in order to allow the positioning and articulation of a femoral prosthesis.

Anchoring the insert inside the acetabular cup can be done for example usually by a conical coupling between the internal surface of the acetabular cup and the external surface of the acetabular insert, which generally allows an adequately stable connection.

One possible disadvantage of these embodiments is that during the surgical operation to insert the prosthesis, the conditions of space and visibility are not always able to allow a simple and correct positioning of the insert in the acetabular cup. In fact, typically, the conical coupling is self-centering only for very limited angular deviations with respect to a correct and centered position, whereas if said angular deviations are greater, there may be a cross-positioning between cup and insert. Consequently, the coupling may take place, but erroneously, with possibly serious consequences for the patient, for example dislocation, breakage of the insert, if made of fragile material, or again the cup may come out.

Another disadvantage can occur during the step of attaching the cup to the pelvis, since there may be a deformation of the material of the cup which can lead to an erroneous coupling of the insert, with a consequent possible cross-positioning thereof.

It is also known that to facilitate the positioning operations of the insert, a centering pin can be used, and a suitable centering hole on the acetabular cup.

The combination of the centering pin and hole together obtains a centering guide that during the positioning step allows the centering of the contact surfaces of cup and insert.

Generally, between the centering pin and the hole a difference in diameter is provided, although minimal, which allows the insertion of the pin into the centering hole, and also provides for production tolerances. The smaller the difference in diameter, the smaller the possibility of an erroneous positioning at the moment of insertion.

One possible disadvantage of embodiments with centering hole and pin, which can be particular important if the insert is made of fragile materials, for example it may be a ceramic material, can be that the edge of the pin, in contact with the surface of the insert, can be subject to breakages or chipping.

This disadvantage can occur, in particular, if the pin comes into contact with the edge of the centering hole near the internal surface of the acetabular cup.

A prosthetic element is known, for example from US-A-2012/0101590, having an insert for an acetabular cup provided with a centering pin with an inverse conical shape or truncated cone shape, tapered from the outside toward the inside of the insert, with the edge of the pin in contact with the surface of the insert, which is rounded. The diameter of the centering pin at the end facing toward the pole of the insert is less than the diameter at the end of the guide pin facing in the opposite position to the pole of the insert. The centering hole can have a tapered configuration from the inside to the outside of the acetabular cup.

Document U.S. Pat. No. 7,267,693 is also known, which describes a clamping ring for a lining of an acetabular cup. The acetabular cup is provided with a hole at the top, closed by an upper lining cone, when the latter is fixed inside the acetabular cup by the clamping ring.

One possible disadvantage of this embodiment is that even an upturned cone conformation can have the risk of chipping, for example following possible sudden variations in inclinations of the insert when the centering pin is already inside the corresponding hole.

A possible further disadvantage of this form of embodiment is that it is less simple to insert the pin into the hole, because the contact surfaces thus obtained are not adapted to reduce friction between pin and housing.

A purpose of the present invention is to obtain an acetabular prosthesis, in particular used for a hip prosthesis, that facilitates the insertion and centering of the insert in the acetabular cup, even in the event of inclinations subsequent to the insertion of the pin.

The Applicant has devised, tested and embodied the present invention to overcome the shortcomings of the state of the art and to obtain these and other purposes and advantages.

SUMMARY OF THE INVENTION

The present invention is set forth and characterized in the independent claims, while the dependent claims describe other characteristics of the present invention or variants to the main inventive idea.

In accordance with the above purpose, an acetabular prosthesis according to the present invention which overcomes the limits of the state of the art and eliminates the defects therein, comprises:
- an acetabular cup;
- an acetabular insert, configured to be stably coupled inside the acetabular cup and to receive the articulation head of a femoral prosthesis or of a natural femur;
- a centering unit configured to guide and center the insertion and stable positioning of the acetabular insert in the acetabular cup.

The centering unit comprises a centering hole provided in the acetabular cup and a centering pin provided on the acetabular insert and which develops along a centering axis, configured to be inserted in the centering hole.

According to the present invention, the centering pin is provided with an external lateral surface that has an undulating development or profile along the centering axis with at least one concave part followed by at least one convex part, wherein the concave part is continuously connected to the convex part by a connection inflection. Therefore the shape of the centering pin according to the present description does not provide conical or truncated cone shapes.

This undulating configuration of the centering pin with the concave part connected to the convex part can make the insertion and centering of the insert in the acetabular cup easier, even in the case of inclinations subsequent to the insertion of the pin.

The present invention also concerns an acetabular insert configured to be stably coupled to the inside of the acetabular cup of an acetabular prosthesis and to receive an articulation head.

The acetabular insert comprises a centering pin which develops along a centering axis, configured to be inserted in a centering hole of the acetabular cup to define a centering unit configured to guide and center the insertion and stable positioning of the acetabular insert in the acetabular cup.

According to the present invention, the centering pin is provided with an external lateral surface that has an undulating development or profile along the centering axis with at least one concave part followed by at least one convex part, wherein the concave part is continuously connected to the convex part by a connection inflection.

These and other aspects, characteristics and advantages of the present disclosure will be better understood with reference to the following description, drawings and attached claims. The drawings, which are integrated and form part of the present description, show some forms of embodiment of the present invention, and together with the description, are intended to describe the principles of the disclosure.

The various aspects and characteristics described in the present description can be applied individually where possible. These individual aspects, for example aspects and characteristics described in the attached dependent claims, can be the object of divisional applications.

It is understood that any aspect or characteristic that is discovered, during the patenting process, to be already known, shall not be claimed and shall be the object of a disclaimer.

BRIEF DESCRIPTION OF THE DRAWINGS

These and other characteristics of the present invention will become apparent from the following description of some forms of embodiment, given as a non-restrictive example with reference to the attached drawings wherein.

To facilitate comprehension, the same reference numbers have been used, where possible, to identify identical common elements in the drawings. It is understood that elements and characteristics of one form of embodiment can conveniently be incorporated into other forms of embodiment without further clarifications.

DETAILED DESCRIPTION OF THE FORMS OF EMBODIMENT

We shall now refer in detail to the various forms of embodiment of the present invention, of which one or more examples are shown in the attached drawings. Each example is supplied by way of illustration of the invention and shall not be understood as a limitation thereof. For example, the characteristics shown or described insomuch as they are part of one form of embodiment can be adopted on, or in association with, other forms of embodiment to produce another form of embodiment. It is understood that the present invention shall include all such modifications and variants.

Figures 1, 2:
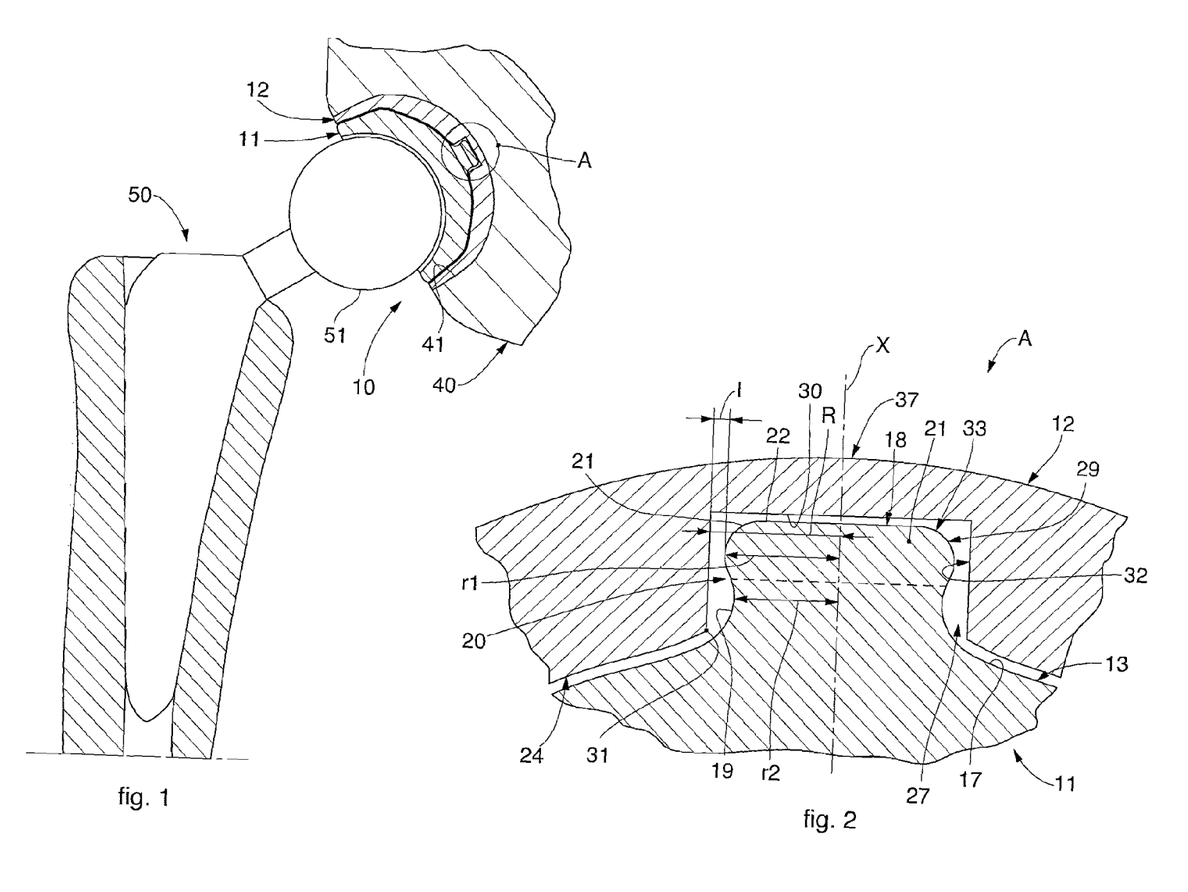
FIG. 1 is a partial section of an acetabular prosthesis according to forms of embodiment described here, joined to a femoral prosthesis.
FIG. 2 is an enlarged detail of FIG. 1.

FIG. 1 is used to describe forms of embodiment of an acetabular prosthesis 10 according to the present invention, which can be used for a hip prosthesis and comprises an acetabular cup 12 and an acetabular insert 11 configured to be stably coupled inside the acetabular cup 12 and to receive the articulation head 51 of a femoral prosthesis 50 or also of a natural femur, which can typically be essentially spherical in shape.

Typically the acetabular prosthesis 10 is suitable to be inserted, for example, inside a cotyloid acetabulum 41 of the iliac bone 40, functioning as a positioning and rotation seating for the articulation head 51.

Figure 3:
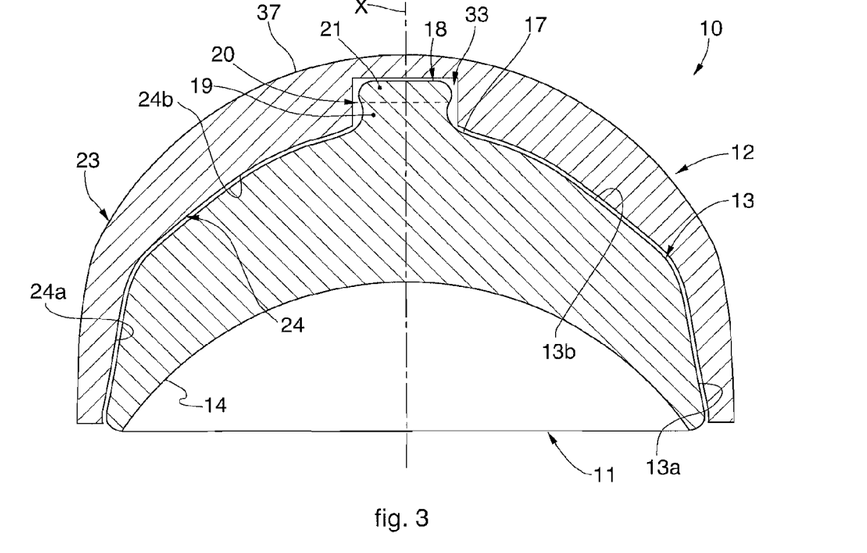
FIG. 3 is a cross section of an acetabular prosthesis according to forms of embodiment described here.

In possible forms of embodiment, described for example with reference to FIG. 3, the acetabular insert 11 can have an axial symmetry around a centering axis X. Typically, in a coordinated way, the acetabular cup 12 can also be symmetrical with respect to the centering axis X, common to the acetabular insert 11.

In possible forms of embodiment, the acetabular insert 11 can be made of a material having great hardness, in order to resist wear for example due to the movement of the articulation head 51. Some examples of suitable materials can be metal alloys with a cobalt base, for example an alloy of chromium-cobalt-molybdenum, or biocompatible ceramic or polyethylene, preferably with a high or very high reticulation.

In possible forms of embodiment, the acetabular cup 12 can be made of an osteo-compatible metal material, for example an alloy of titanium or cobalt.

The acetabular cup 12 is typically configured to be housed inside the cotyloid acetabulum 41. Moreover, the acetabular cup 12 is configured to receive the acetabular insert 11 inside it. Typically, therefore, the acetabular cup 12 can be externally convex and internally concave.

For example, in possible implementations, the acetabular cup 12 can have an external surface of the cup 23 shaped so as to mate to the seating defined by the cotyloid acetabulum 41, for example a spherical cap shape.

Moreover, the acetabular insert 11 is configured to achieve a conical coupling with the acetabular cup 12. For example, in possible implementations, the acetabular insert 11 has an external surface of the insert 13 at least partly shaped like a truncated cone, for example comprising a truncated-cone annular band 13a and a cap-like portion 13b that extends from the truncated-cone annular band 13a and defines a polar zone 17 of the insert, opposite the truncated-cone annular band 13a. In a coordinated way, the acetabular cup 12 has an internal surface of the cup 24 at least partly shaped like a truncated cone, mating with the external surface of the insert 13, comprising for example a truncated-cone annular band 24a and a cap-like portion 24b that extends from the truncated-cone annular band 24a and defines a polar zone 37 of the cup, opposite the truncated-cone annular band 24a. Typically, the conical coupling is achieved between the truncated-cone annular band 13a of the acetabular insert 11 and the truncated-cone annular band 24a of the acetabular cup 12.

Moreover, the acetabular insert 11 is configured to receive the articulation head 51 inside it, and to allow the necessary rotation so as to reproduce the natural movements of rotation and articulation of the hip. For example, in possible implementations, the acetabular insert 11 has an internal surface of the insert 14 that essentially defines a spherical cap mating with the shape of the articulation head 51.

In some forms of embodiment, the acetabular prosthesis 10 comprises a centering unit 33 configured to guide and center the insertion and stable positioning of the acetabular insert 11 in the acetabular cup 12.

FIG. 2 is used to describe forms of embodiment combinable with all the forms of embodiment described here, of the centering unit 33. For example, the centering unit 33 can comprise a centering pin 18 which develops along the centering axis X and is provided protruding from the acetabular insert 11, in particular protruding from the external surface of the insert 13, for example typically disposed in correspondence with the polar zone 17 of the acetabular insert 11. In some forms of embodiment, the centering unit 33 also comprises a centering hole 27 provided in the acetabular cup 12 and configured to receive the centering pin 18, typically made for example in correspondence to the polar zone 37 of the acetabular cup 12. In possible implementations, the centering hole 27 can be blind, and therefore made internally, that is, on the internal surface of the cup 24. In this case, the centering hole 27 can be delimited by a lateral wall 32 which has an external edge 31 and by a bottom 30. In other implementations, the centering hole 27 can be through, that is, made through all the thickness of the acetabular cup 12.

Typically, the centering pin 18 can develop along the centering axis X which is aligned with the axis of the centering hole 27, once the acetabular insert 11 and the acetabular cup 12 have been coupled in a centered manner.

In accordance with forms of embodiment described here, the centering pin 18 is provided with an external lateral surface or shell 29, which has an undulating development or profile along the centering axis X.

By the term "undulating" we mean that the external lateral surface or shell 29 has a more or less regularly sinuous development, with alternate ridges and recesses.

In particular, in example embodiments, the external lateral surface or shell 29 has at least one concavity or concave part 19, which extends from the acetabular insert 11, followed by at least one convexity or convex part 21.

In particular the convex part 21 follows the concave part 19 in the axial direction, defining, in particular, the axially undulated development of the centering pin 18. Consequently, it can be provided that the centering pin 18 has a cross section which axially, in the direction from the inside toward the outside, is provided with a concave-convex development. In other words, the cross section of the centering pin 18 has a concave section defining the concave part 19, which departs toward the outside from the external surface of the insert 13, followed by a convex section, defining the convex part 21. The concave part 19 is therefore at the pole of the acetabular insert 11, while the convex part 21 is in the opposite position to the pole.

Furthermore, in example embodiments, the axial development or profile of the cross section of the centering pin 18 can be defined undulating, in which a groove (concave part 19) is followed by a ridge (convex part 21). In possible example embodiments, the concave part 19 is connected in a continuous way to the convex part 21, for example a connection inflection 20 can be provided. By inflection we mean an inflecting point or localized or accentuated bend or curvature, in particular in which a curve, in passing from one part of the inflection to the other, changes its concavity into convexity and vice versa. According to the present description therefore, the centering pin 18 is not a conical shape nor a truncated cone shape.

In specific examples, the external lateral surface or shell 29 can have a single concavity or concave part 19, followed downstream, along the centering axis X, by a single convexity or convex part 21.

The part of the centering pin 18 that is distal with respect to the external surface of the insert 13 can have a top connection surface 22. In other words, the top surface 22 defines, with respect to the cross section of the centering pin 18, an essentially rectilinear segment that connects the two convex parts 21 on one side and the other with respect to the centering axis X. For example, the top surface 22 can be flat, or circular, curved, beveled or mushroom-shaped or other conformations.

In forms of embodiment described with reference for example to FIG. 2, the centering pin 18 can therefore have a concave/convex development, that is, with at least an inversion of concavity, according to the centering axis X. In particular, as can be seen for example in FIG. 2, the concave part 19 projects from the polar zone 17 and initially tapers off toward the top in order to then flare out, until it reaches the inflection 20, in which the concavity changes into convexity. The convex part 21 develops from the inflection 20, initially flares and then tapers off, always in the axial direction, that is, from the polar zone 17 toward the outside of the acetabular insert 11 until it meets the flat surface 22.

Moreover, in examples described using FIG. 2, the centering hole 27 can be cylindrical, that is, with a circular section, with a smaller radius R, in this case constant for example along the centering axis X.

In possible forms of embodiment, for example described with reference to FIG. 2, the convex part 21 of the centering pin 18 can be provided with a greater radius r1 that represents the widest part of the whole centering pin 18. The difference between the greater radius r1 of the acetabular insert 11 and the smaller radius R of the acetabular cup 12 defines a minimal difference in radius I.

The minimal difference in radius I can be correlated with the guide and centering capacity of the centering unit 33.

Typically, the more the minimum difference in radius I is reduced or minimized, the greater the stability in the positioning of the acetabular insert 11 in the acetabular cup 12, therefore preventing possible incorrect sliding, unwanted cross-positioning or blocking of the acetabular insert 11 inside the acetabular cup 12.

Moreover, typically, a minimum difference of reduced or minimized radius I can be advantageous for example in a first step of inserting the centering pin 18 in the centering hole 27, since, as the centering pin 18 advances axially along the centering hole 27 during the insertion, the possibility of incorrect sliding or cross-positioning is progressively reduced.

We therefore believe that the concave/convex configuration of the centering pin 18 allows the maintenance of a reduced minimum difference in radius I in the upper part of the centering pin 18 and then to have a reduced smaller radius r2 in the lower part of the centering pin 18. The advantage of having a smaller radius r2, reduced in the lower part of the centering pin 18, may be that the probability is reduced of possible collisions between the external edge 31 of the centering hole 27 present on the internal surface of the cup 24 and the base of the centering pin 18. Furthermore, because of the concave-convex configuration of the centering pin 18, between it and the polar zone 17 there are no sharp edges, and the possibility of chipping is reduced. The transition between the concave part 19 with radius r2 and the convex part 21 with radius r1, bigger than r2, is defined by the connection inflection 20.

Figure 4:
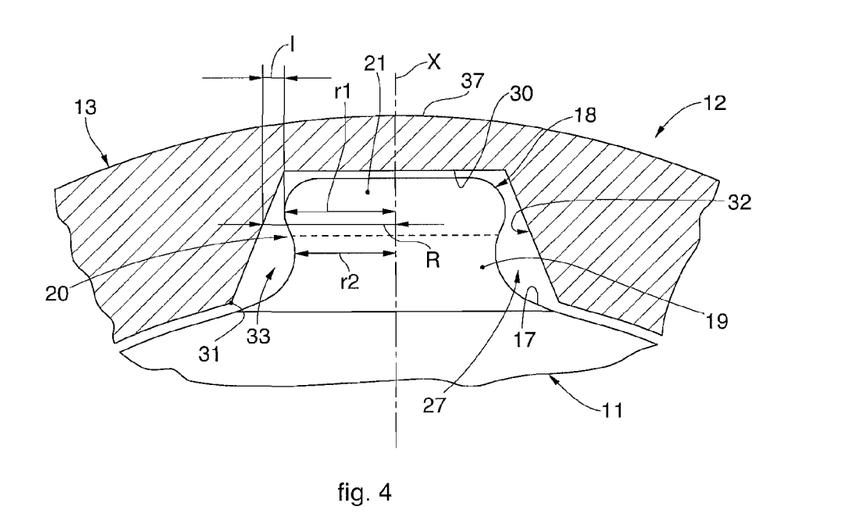
FIG. 4 is a detail of another form of embodiment of an acetabular prosthesis.
Figure 5:
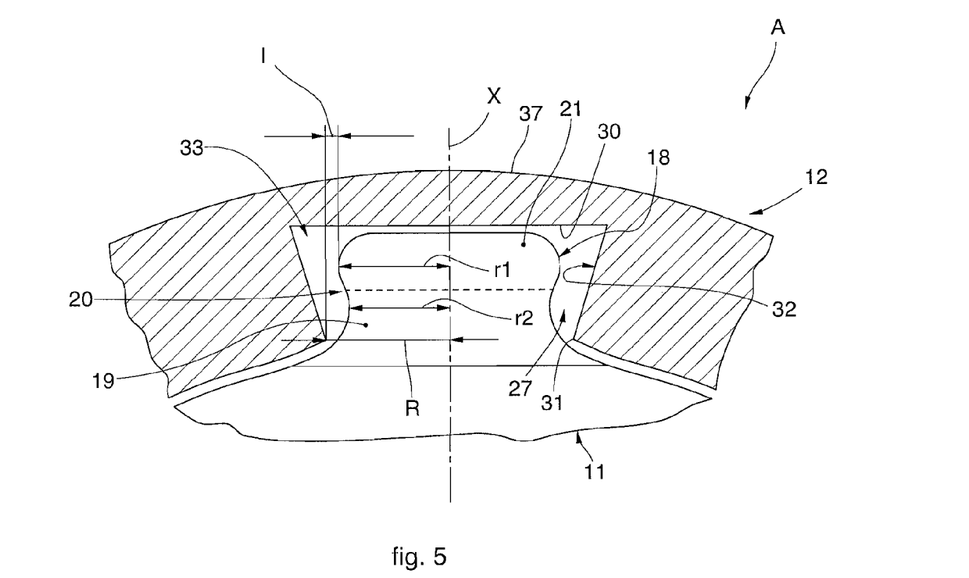
FIG. 5 is a detail of another form of embodiment of an acetabular prosthesis.

In possible implementations, described for example using FIGS. 4 and 5, the centering hole 27 can be a truncated cone shape. For example, the truncated cone shape of the centering hole 27 can be tapered, as can be seen for example in FIG. 4, or flared, as can be seen for example in FIG. 5, in both cases with reference to the direction of the centering axis X, in the direction from inside to outside the acetabular cup 12.

According to the forms of embodiment described here, the conformation of the centering pin 18 configured concave-convex can allow an insertion with fewer risks of chipping the surface of the centering pin 18 itself.

Indeed, a curvilinear or undulating development of the centering pin 18 can define a contact surface that facilitates the sliding of the lateral wall 32 of the centering hole 27, but at the same time, due to the reduced or minimized minimum difference in radius I in the upper part of the centering pin 18, the guiding effect of the centering unit 33 is adequately maintained.

Figure 6:
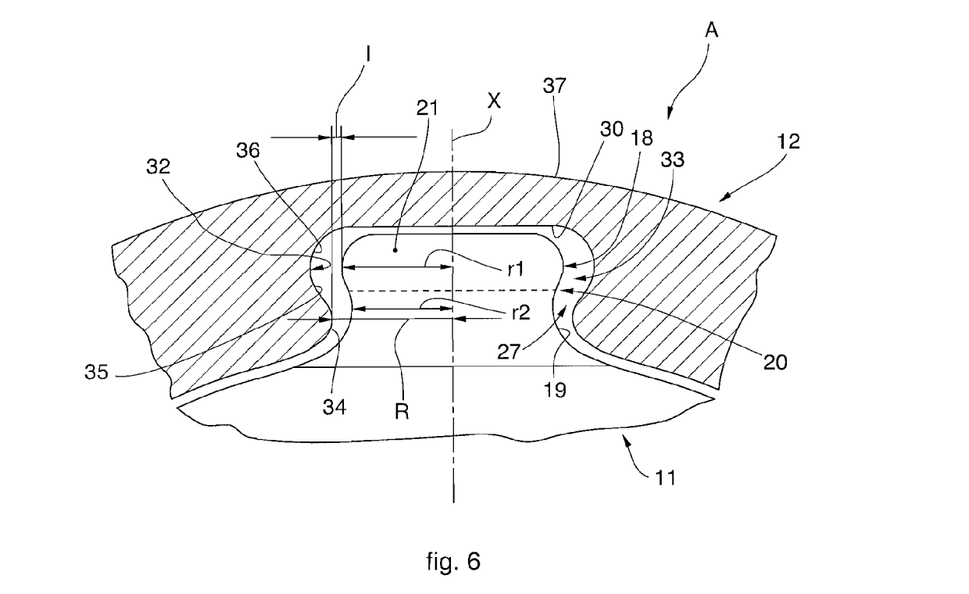
FIG. 6 is a detail of another form of embodiment of an acetabular prosthesis.

In other forms of embodiment, described for example with reference to FIG. 6, the centering hole 27 can have a convex-concave conformation, that is, an inversion of the concavity, along the centering axis X, for example quite opposite to the concave-convex configuration of the centering pin 18. That is to say, the centering hole 27 can have a more inwardly convex part 34 and a more outwardly concave part 36. For example, to this end the lateral wall 32 of the centering hole 27 can be suitably undulating in shape. In particular, in this case the development of the lateral wall 32 can have a narrowing—convex part 34—near to the internal surface of the cup 24, as far as the smaller radius R, and can then widen—concave part 36—for example by means of an inflection 35 in which the inversion of concavity is provided.

One possible advantage of the forms of embodiment described for example with reference to FIG. 6 is that a minimum difference in radius I can be maintained, reduced in the initial part of the insertion and also the external edge 31 is beveled or eliminated, instead defining a curved, rounded, convex or beveled surface, such as for example the surface of the convex part 34. This can further reduce the probability of chipping, adding to the same effect produced by the narrowing of the centering pin 18 in its concave part 19. Furthermore, the meeting of the curvilinear surfaces present both in the centering pin 18 and in the centering hole 27 can produce a facilitated sliding along the centering axis, advancing toward the bottom 30 of the centering hole 27.

In other examples, the centering hole 27 can have a curvilinear shape.

Figure 7:
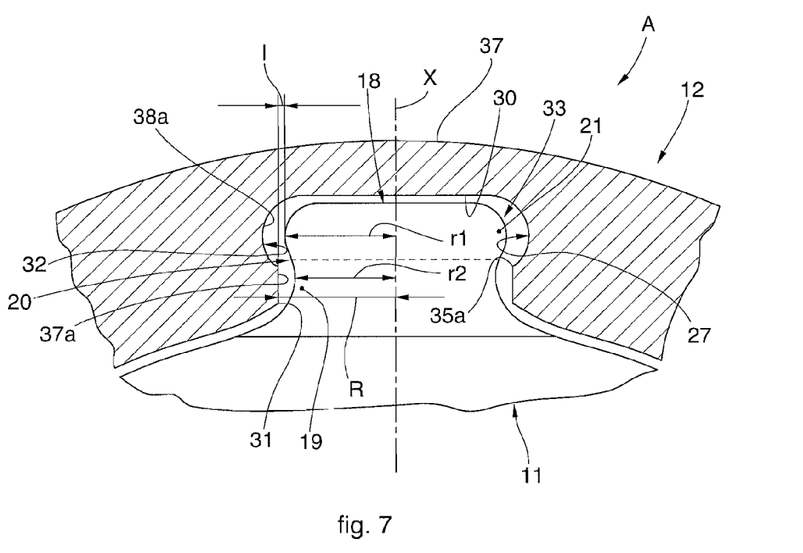
FIG. 7 is a detail of yet another form of embodiment of an acetabular prosthesis.
Figure 8:
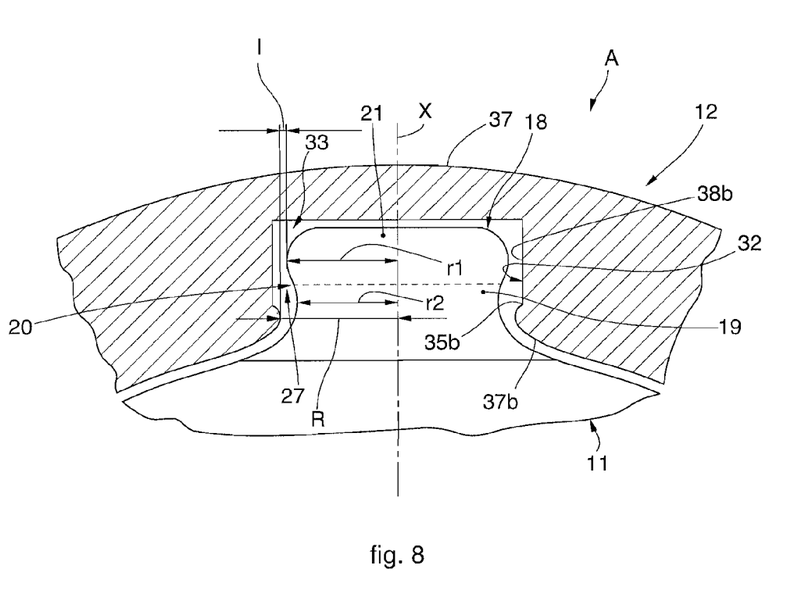
FIG. 8 is a detail of another form of embodiment of an acetabular prosthesis.

In other forms of embodiment, described for example with reference to FIGS. 7 and 8, the centering hole 27 can have a section with a mixed configuration along the centering axis X, that is, combined linear and curvilinear, for example defined by a cylindrical portion and a concave or convex portion.

The example forms of embodiment described using FIGS. 7 and 8 can allow constructional simplicity, due to the presence of a linear segment in the cylindrical part, typically easier to produce. Moreover, the guide and centering advantages connected to the minimum reduced difference in radius I as discussed above are in any case maintained.

In possible implementations, with reference for example to FIG. 7, the centering hole 27 can have a cylindrical part toward the inside of the acetabular cup 12 and a concave part toward the outside. For example, the lateral wall 32 of the centering hole 27 can have a cylindrical part 37a and a concave part 38a, for example connected by an inflection 35a.

In possible implementations, with reference for example to FIG. 8, the centering hole 27 can have a convex part 37b toward the inside of the acetabular cup 12 and a cylindrical part 38b toward the outside. For example, the lateral wall 32 of the centering hole 27 can have a first convex part 37b and a second cylindrical part 38b, for example connected by an inflection 35b. This form of embodiment, having the external edge 31 beveled or eliminated in favor of a curved, rounded or convex surface, can also reduce the probability of chipping, as discussed for example with reference to FIG. 6.

It is clear that modifications and/or additions of parts may be made to the acetabular prosthesis 10 as described heretofore, without departing from the field and scope of the present invention.

It is also clear that, although the present invention has been described with reference to some specific examples, a person of skill in the art shall certainly be able to achieve many other equivalent forms of acetabular prosthesis, having the characteristics as set forth in the claims and hence all coming within the field of protection defined thereby.

The invention claimed is:

1. Acetabular prosthesis comprising:
   an acetabular cup;
   an acetabular insert, configured to be stably coupled inside the acetabular cup and to receive an articulation head;
   a centering unit configured to guide and center the insertion and stable positioning of the acetabular insert in the acetabular cup, said centering unit comprising a centering hole provided in the acetabular cup, the centering hole having a minimum radius R, and a centering pin provided on the acetabular insert and which develops along a centering axis, configured to be inserted in the centering hole,
   wherein the centering pin is provided with an external lateral surface that has an undulating profile along the centering axis,
   wherein the undulating profile is continuous and includes a concave part and a convex part connected by a connection inflection,
   wherein the centering pin has a maximum radius R1 coinciding with the convex part, with the maximum radius R1 being less than the minimum radius R, and
   wherein at least a portion of the convex part is disposed above the maximum radius R1 adjacent a top surface of the centering pin and defines a contact surface arranged to guide and center the centering pin upon first inserting the centering pin into the centering hole.

2. Acetabular prosthesis as in claim 1, wherein the centering pin protrudes externally from the acetabular insert, the concave part developing from the acetabular insert and the convex part being downstream of the concave part with respect to the acetabular insert.

3. Acetabular prosthesis as in claim 1, wherein said acetabular insert and said acetabular cup have axial symmetry around said centering axis.

4. Acetabular prosthesis as in claim 1, wherein the centering pin is disposed in a polar zone of the acetabular insert and the centering hole is provided in a polar zone of the acetabular cup.

5. Acetabular prosthesis as in claim 1, wherein the acetabular insert is configured to achieve a conical coupling with the acetabular cup.

6. Acetabular prosthesis as in claim 5, wherein the acetabular insert has an external surface of the insert at least partly shaped like a truncated cone, and the acetabular cup has an internal surface of the cup at least partly shaped like a truncated cone, mating with the external surface of the insert.

7. Acetabular prosthesis as in claim 6, wherein the external surface of the insert comprises a truncated-cone annular band and a cap portion that extends from the truncated-cone annular band, and the internal surface of the cup comprises a truncated-cone annular band and a cap portion that extends from the truncated-cone annular band.

8. Acetabular prosthesis as in claim 1, wherein the centering hole is blind or is through.

9. Acetabular prosthesis as in claim 1, wherein a lower extent of the centering hole defines an external edge and the acetabular insert includes a polar region, and wherein the centering pin further includes a reduced radius R2 coinciding with the concave part and disposed below the maximum radius R1 and adjacent the polar region, the reduced radius R2 sized to avoid contact with the external edge.

10. Acetabular prosthesis comprising:
   an acetabular cup;
   an acetabular insert configured to be coupled inside the acetabular cup and to receive an articulation head;
   a centering unit configured to guide and center the insertion and positioning of the acetabular insert in the acetabular cup, the centering unit comprising a centering hole provided in the acetabular cup, the centering hole having an exclusively straight and linear lateral sidewall, and a centering pin provided on the acetabular insert and which develops along a centering axis, the centering pin configured to be inserted in the centering hole;
   the centering pin including an external lateral surface having a continuously curved undulating profile along the centering axis, the undulating profile including a concave part and a convex part, the concave part and the convex part directly connected by a connection inflection without an intervening straight section between the concave part and the convex part;
   the centering pin having a maximum radius R1, the maximum radius R1 coinciding with the convex part, the maximum radius R1 of the centering pin sized to form a size difference clearance with respect to the straight lateral sidewall of the centering hole; and
   wherein at least a portion of the convex part is disposed above the maximum radius R1 adjacent a top surface of the centering pin and defines a curved contact surface arranged to guide and center the centering pin upon first inserting the centering pin into the centering hole.

11. Acetabular prosthesis as in claim 10, wherein the acetabular insert includes a polar region, and wherein a lower extent of the lateral sidewall defines an external edge, and further wherein the centering pin further includes a reduced radius R2 coinciding with the concave part and disposed below the maximum radius R1 and adjacent the polar region, the reduced radius R2 sized to avoid contact with the external edge.

* * * * *